(12) United States Patent
Zhu et al.

(10) Patent No.: US 7,586,024 B2
(45) Date of Patent: Sep. 8, 2009

(54) METHOD FOR CULTIVATING TRANSGENIC PLANTS WITH HIGH VIRUS RESISTANCE AND THE USE THEREOF

(75) Inventors: Zhen Zhu, Beijing (CN); Dejiang Feng, Beijing (CN); Xiang Liu, Beijing (CN)

(73) Assignee: Institue of Genetics and Developmental Biology, Chinese Adacemy of Sciences, Beijing (CN)

( * ) Notice: Subject to any disclaimer, the term of this patent is extended or adjusted under 35 U.S.C. 154(b) by 390 days.

(21) Appl. No.: 10/542,855

(22) PCT Filed: Jan. 19, 2004

(86) PCT No.: PCT/CN2004/000069

§ 371 (c)(1), (2), (4) Date: Mar. 31, 2006

(87) PCT Pub. No.: WO2004/065597

PCT Pub. Date: Aug. 5, 2004

(65) Prior Publication Data

US 2006/0212967 A1    Sep. 21, 2006

(30) Foreign Application Priority Data

Jan. 21, 2003    (CN) .............................. 03 1 00708

(51) Int. Cl.
C12N 15/82    (2006.01)
C12N 15/87    (2006.01)

(52) U.S. Cl. ...................... 800/280; 800/279; 800/278; 435/320.1

(58) Field of Classification Search ........................ None
See application file for complete search history.

(56) References Cited

FOREIGN PATENT DOCUMENTS

WO    WO 02/083925    10/2002

OTHER PUBLICATIONS

Van Hoof et al. 1997, Plant Molecular Biology 35:383-387.*

Dejiang Feng et al., "Silencing of Potato Virus X Coat Protein Gene in Transgenic Tobaccos by Codon Replacement That Confers Resistance to PVX Infection," Chinese Science Bulletin, vol. 48, No. 12, Jun. 30, 2003, pp. 1308-1314.
E. Jay De Rocher et al., 1998, Plant Physiol. 117:1445-1461.
Covey, SN, 1997, Nature, 385(27): 781-782.
C. Napoli et al., 1990, Plant Cell, 2:279-289.
Van der Krol Ar et al., 1990, Plant Cell, 2:291-299.
M. T. Ruiz et al., 1998, Plant Cell, 10(6): 937-946.
T. Dalmay et al., 2000, Plant Cell, 12(3): 369-379.
K. M. Land, 2001, Trends in Genetics, 17(7): 379.
L. Jones et al., 1999, Plant Cell, 11(12): 2291-301.
R. A. Burton et al., 2000, Plant Cell, 12(5): 691-706.
F.G. Ratcliff et al., 1999, The Plant Cell, 11, 1207-1215.
O. Voinnet, Trends in Genet, 17:449-459.
M. A. Matke et al., 2002, Adv Genet, 46-235-75.
R. Plasterk, H. Science, 2002, 17:296 (5571):1263-5.
D. C. Baulcombe, Trends Microbiol., 2002, 10(7): 306-8.
T. Ikemura, 1985, Mol. Biol. Evol., 2-13-35.
M. A. Antezana, 1999, J Mol Evol, 49 (1):36-43).
T. Kleber-Janke et al., 2000, Protein Expr Purif, 19:419-424.
D. Bregeon et al., 2001, Genes Dev, 15:2295-306.
Chen, GFT et al., 1990, Nucl Acids Res. 18:1465-1473.
A. Hoekema et al., 1987, Mol. Cell. Biol. 7:2914-2924.

* cited by examiner

*Primary Examiner*—Stuart F. Baum
*Assistant Examiner*—Li Zheng
(74) *Attorney, Agent, or Firm*—Morgan, Lewis & Bockius LLP (57) ABSTRACT

The invention discloses a method for breeding transgenic plants with the high antiviral property and the application of the method. The inventive method comprises the following steps of: a. checking the frequency of codon usage in a host and determining the rare codons in the host, modifying the codons in a target gene so that some codons in the target gene are mutated into the rare synonymous codons in the host plant; b. constructing a vector containing the target gene with the codon modifications, to be used for transforming plants; c. transforming the plants with the above recombinant vector to obtain the regenerative transgenic plants; d. detecting the transformed plants, screening the transgenic plants in which gene silencing occurs in the target gene, and thereby obtaining the transgenic plants with the high antiviral property. The invention method can be used in breeding highly efficient and stable antiviral transgenic plants.

5 Claims, 5 Drawing Sheets

```
  1  gctctagagATG TCA GCA CCA GCT AGC ACA ACA CAG CCC ATA GGG TCA ACT ACC TCA    Xba I
              M   S   A   P   A   S   T   T   Q   P   I   G   S   T   T   S
                                       G   G   G           G                    Pst I
 48  ACT ACC ACA AAA ACT GCA GGC GCA ACT CCT GCC ACA GCT TCA GGC CTG             Stu I
      T   T   T   K   T   A   G   A   T   P   A   T   A   S   G   L
 96  TTC ACC ATC CCG GAT GGG GAT TTC TTT AGT ACA GCC CGT GCC ATA GTA
      F   T   I   P   D   G   D   F   F   S   T   A   R   A   I   V
144  GCC AGC AAT GCT GTC GCA ACA AAT GAG GAC CTC AGC AAG ATT GAG GCT
      A   S   N   A   V   A   T   N   E   D   L   S   K   I   E   A
196  ATT TGG AAG GAC ATG AAG GTG CCC ACA GAC ACT ATG GCA CAG GCT GCT
      I   W   K   D   M   K   V   P   T   D   T   M   A   Q   A   A
244  TGG GAC TTA GTC AGA CAC TGT GCT GAT GTA GGA TCA TCC GCT CAA ACA
      W   D   L   V   R   H   C   A   D   V   G   S   S   A   Q   T
292  GAA ATG ATA GAT ACA GGT CCC TAT TCC AAC GGC ATC AGC AGA GCT AGA
      E   M   I   D   T   G   P   Y   S   N   G   I   S   R   A   R
                                       G   G   G
340  CTG GCA GCA GCA ATT AAA GAG GTG TGC ACA CTT AGG CAA TTT TGC ATG             ApaL I
      L   A   A   A   I   K   E   V   C   T   L   R   Q   F   C   M
                                                   G       TCG   G
388  AAG TAT GCT CCA GTG GTA TGG AAC TGG ATG TTA ACT AAC AAC AGT CCA             Hpa I
      K   Y   A   P   V   V   W   N   W   M   L   T   N   N   S   P
       G   G
436  CCT GCT AAC TGG CAA GCA CAA GGT TTC AAG CCT GAG CAC AAA TTC GCT
      P   A   N   W   Q   A   Q   G   F   K   P   E   H   K   F   A
484  GCA TTC GAC TTC TTC AAT GGA GTC ACC AAC CCA GCT GCC ATC ATG CCC
      A   F   D   F   F   N   G   V   T   N   P   A   A   I   M   P
532  AAA GAG GGG CTC ATC CGG CCA CCG TCT GAA GCT GAA ATG AAT GCT GCC
      K   E   G   L   I   R   P   P   S   E   A   E   M   N   A   A
580  CAA ACT GCT GCC TTT GTG AAG ATT ACA AAG GCC AGG GCA CAA TCC AAC
      Q   T   A   A   F   V   K   I   T   K   A   R   A   Q   S   N
628  GAC TTT GCC AGC CTA GAT GCA GCT GTC ACT CGA GGT CGT ATC ACT GGA
      D   F   A   S   L   D   A   A   V   T   R   G   R   I   T   G
676  ACA ACA ACC GCT GAG GCT GTT GTC ACT CTA CCA CCA CCA TAA  ggtacccc           Kpn I
      T   T   T   A   E   A   V   V   T   L   P   P   P   ---
```

Fig. 10

METHOD FOR CULTIVATING TRANSGENIC PLANTS WITH HIGH VIRUS RESISTANCE AND THE USE THEREOF

FIELD OF THE INVENTION

The present invention relates to a method for breeding transgenic plants and the applications of them, and more particularly, to a method for breeding transgenic plants with high antiviral property and the applications of them.

BACKGROUND OF THE INVENTION

Plant virus is one of the major diseases in the crop production. Sometimes, plant virus may impact a catastrophic influence on the agricultural production. Breeding transgenic plants with high antiviral property is a hot point in the biology researches.

The studies in recent years find that the gene silencing mechanism is one of the plant defense mechanisms, through which plants resist the invasion of virus (Covey, S N, 1997, Nature, 385(27): 781-782). The phenomenon of gene silencing was firstly found by Napoli, in conducting the research of the gene chs encoding Chalcone synthase (CHS) in petunia in 1990. (Napoli C, et al. 1990, Plant Cell, 2: 279-289; Van der Krol Ar, et al. 1990, Plant Cell, 2:291-299). Not only the expression of the exogenous chs gene, and but also the expression of the endogenous chs gene is silenced. This phenomenon is called co-suppression. It finds that the phenomenon of gene silencing occurs not only in the transformed gene or transgene, but also in the endogenous gene of the host. The gene is silenced by the induction of the transgene or virus (Ruiz M T, et al., 1998, Plant Cell, 10(6): 937-946; Dalmay T, et al., 2000, Plant Cell, 12(3): 369-379). The phenomenon of gene silencing widely exists in plants, animals, bacteria and fungi (Land, K M. 2001, Trends in Genetics, 17 (7): 379).

Studies find that the "recovery" phenomenon may occur in the plant by transformation of virus gene. It finds that the newly emerging leaves of the transgenic plants infected by a virus have the resistance against the virus. At the same time, the transgene contained in the plant is silenced (Covey, S N, et al. 1997, Nature, 385(27):781-782). Further, when a plant is infected with a virus carrying a plant gene, the corresponding endogenous gene of the plant can also be silenced (Jones L, et al. 1999, Plant Cell, 11(12): 2291-301; Burton R A, et al. 2000, Plant Cell, 12(5): 691-706). When a transgenic plant contains a transgene not derived from viruses and plants, and the transgenic plant is infected with a virus carrying such a gene, the gene can also be silenced. Thus, virus is an object of gene silencing, as well as is an induction factor for producing the gene silencing (Ratcliff, F G. et al. 1999, The Plant Cell, 11, 1207-1215). Plants will activate the gene silencing mechanism when being infected by a virus, making the virus not to propagate in vivo. In this way, the plants will exhibit the immunity or high resistance. The post-transcriptional gene silencing is an immune mechanism for plants to fight against the invasion of virus. (Voinnet, O. 2001, Trends in Genet, 17:449-459; Matzke, M A. et al, 2002, Adv Genet, 46:235-75; Plasterk R H. Science, 2002, 17; 296(5571): 1263-5; Baulcombe D C, Trends Microbiol, 2002, 10(7): 306-8).

The researches of gene silencing mechanism make it possible that the principle of the gene silencing mechanism can be used in breeding high antiviral transgenic plant. A key problem in the use of gene silencing is how to increase the frequency of gene silencing in a target gene. Although one can use a virus vector to effectively induce the gene inactivation, the limitations of virus vector lead that some of the specific genes in a given host cannot be researched and exploited. In addition, although one can use transformation methods to produce gene silencing, the efficiency of producing gene silencing in the natural condition is low. Thus, if a method for improving the inactivation of target gene in a transgenic host may be provided, the transgenic plant with high antiviral property can be created through this method.

SUMMARY OF THE INVENTION

The object of the present invention is to provide a method for effectively improving the inactivation of a target gene in transgenic hosts, thereby obtaining transgenic plants with a high antiviral property.

A method for obtaining transgenic plants with high antiviral property, comprising the following steps of:
a. checking the frequency of codon usage of a host and determining the rare codons in the host, modifying the codons in a target gene so that some codons in the target gene are mutated into the rare synonymous codons in the host plants;
b. constructing a vector containing the target gene with the codon modifications, to be used for transforming plants;
c. transforming the plants with the recombinant vector, to obtain the regenerative transgenic plants; and
d. detecting the transformed plants, screening the transgenic plants in which gene silencing occurs in the target gene, and thereby obtaining the transgenic plant with high antiviral property.

In order to facilitate the screening, said vector further comprises a selective marker gene.

Said rare codon is the codon of a usage frequency between 0% and 10%.

Said vector may be prokaryotic expression vector, or eukaryotic expression vector.

Generally, checking the usage frequency of the host codons is conducted in GenBank gene database or the like databases.

Said target gene means the gene of research interests and of application values.

Said mutation methods include any of the conventional mutation methods in which the goal is to mutate one or more of the codons in the target gene into the rare synonymous codons, for example, site-directed mutagenesis, etc. The methods for transforming the host include any of the conventional methods in which the exogenous gene can be introduced into the host, such as *Agrobacterium*-mediated transformation, the gene gun method, etc.

The cell lines and the plants obtained according to the methods of the present invention are to be within the protection scope of the invention. The methods of the present invention are of importance in the theory and practice for plant breeding, especially in breeding transgenic plants with a high antiviral property.

The basis of this invention is as follows. There are many tRNA pools in every organism. In other words, each tRNA in the body of an organism exhibits certain abundance. If a certain tRNA is in shortage or is used intensively, the corresponding tRNA pools will become smaller and smaller (Ikemura T. 1985, Mol. Biol. Evol., 2:13-35; Antezana M A, 1999, J Mol Evol, 49(1):36-43). Generally speaking, the tRNA pool of the rare tRNA will more easily become smaller than that of the abundant tRNA. When expressing a panel of peanut allergens in bacteria, it finds that the expression amount of Ara h 1, Ara h 2, and Ara h 6 with an AGA/AGG codon content of 8-10% in the cDNA is much lower than that of Ara h 5 with an AGA/AGG codon content of only 0.8% in the cDNA. In the case of not altering the codon content, if the *E. coli* argU, ileY and lueW genes which code the rare tRNA for arginine are expressed in bacteria, the expression of Ara h 1, Ara h 2 and Ara h 6 with a high content of the rare codon for arginine increases more than 100-fold (Kleber-Janke T, et al. 2000, Protein Expr Purif, 19: 419-424). If the GA-repeat fragment is inserted into the open reading frame (ORF) of lacZ to generate a specific shiftframe mutation, many of the rare codons will be produced. Studies find that the corresponding tRNAs are largely used due to the increase of the rare codons in the gene, leading to an increase of the non-load rate or empty rate in the A site of ribosome which lowers the expression level (Bregeon D, et al. 2001, Genes Dev, 15: 2295-306). Chen et al find that the insertion of four consecutive codons of arginine (Arg) that are used rarely in *E. coli* at the downstream of the LacZ start codon, results in a reduction in the translation efficiency of LacZ. And further, the translation efficiency will increase if increasing the distance between the rare codon and the start codon. One interpretation for this event is that the lack of tRNA in the early phase of translation initiation results in a too long pausing time of the ribosome, thereby producing "traffic jam" and making the ribosome not to be stable. This may easily cause the degradation of mRNA (Chen, G F T., et al. 1990, Nucl Acids Res. 18:1465-1473). It is found that the expression amount is decreased by more than 10-fold when the normal codons in phosphate glycerate kinase (PGK1) of the yeast is replaced with the synonymous least-used codons (Hoekema A., et al. 1987, Mol. Cell. Biol. 7:2914-2924). Similarly, the target gene in the expression vector constructed by use of this method contains a lot of rare codons. When introduced into the host for expression, the corresponding mRNA is easier to be degraded (Rocher E J E. et al. 1998, Plant physiol. 117:1445-1461), and thereby the expression of the target gene will be decreased or even be completely closed.

BRIEF DESCRIPTION OF THE DRAWINGS

FIG. 10 is the gene sequence and the amino acid sequence of PVX coat protein, SEQ ID NO: 1.

DESCRIPTION OF THE PREFERRED EMBODIMENTS

EXAMPLE 1

Codon Modification of the Coat Protein Gene of the Potato Virus X (PVX)

Firstly, check the GenBank and find the values for the usage frequency of all the codons in the tobacco *Nicotiana tabacum* and of all the codons in the coat protein (CP) genes of the potato virus X (PVX). Then, identify the rare codons in tobacco (as shown in table 1).

TABLE 1

Tobacco *Nicotiana tabacum* (T) and the Coat Protein Gene of Potato Virus (P)*

| Amino acid | Condon | Frequency ($10^{-3}$) of condon usage | | Amino acid | Condon | Frequency ($10^{-3}$) of condon usage | | Amino acid | Condon | Frequency ($10^{-3}$) of condon usage | |
|---|---|---|---|---|---|---|---|---|---|---|---|
| | | T | P | | | T | P | | | T | P |
| Arg | CGA | 6.5 | 3.4 | Leu | CUA | 9.2 | 14.7 | Ser | UCA | 17.6 | 13.4 |
| | CGC | 4.0 | 4.4 | | CUC | 10.2 | 18.1 | | UCC | 10.4 | 10.3 |
| | CGG | 3.7 | 3.0 | | CUG | 10.3 | 14.9 | | UCG | 5.2 | 4.0 |
| | CGU | 7.6 | 2.5 | | CUU | 23.9 | 11.2 | | UCU | 20.2 | 9.5 |
| | AGA | 15.4 | 14.8 | | UUA | 12.5 | 11.1 | | AGC | 10.0 | 16.4 |
| | AGG | 12.2 | 15.9 | | UUG | 21.4 | 15.2 | | AGU | 13.1 | 12.0 |
| Ala | GCU | 31.9 | 29.3 | Gly | GGA | 24.0 | 18.1 | Val | GUA | 11.3 | 10.3 |
| | GCA | 22.8 | 28.8 | | GGC | 11.6 | 14.1 | | GUC | 11.4 | 16.1 |
| | GCC | 12.7 | 27.2 | | GGG | 10.5 | 10.3 | | GUG | 16.5 | 19.7 |
| | GCG | 5.8 | 7.9 | | GGU | 23.3 | 11.7 | | GUU | 26.9 | 12.1 |
| Thr | ACA | 17.3 | 29.6 | Pro | CCA | 20.4 | 20.7 | Ile | AUA | 14.4 | 13.1 |
| | ACC | 9.9 | 20.1 | | CCC | 6.8 | 11.9 | | AUC | 13.8 | 24.6 |
| | ACG | 4.5 | 7.0 | | CCG | 4.8 | 8.6 | | AUU | 27.5 | 18.5 |
| | ACU | 21.1 | 26.2 | | CCU | 18.9 | 12.0 | | | | |
| Lys | AAA | 32.0 | 28.3 | Asn | AAC | 18.9 | 23.7 | Glu | GAA | 35.1 | 32.2 |
| | AAG | 33.4 | 37.0 | | AAU | 27.7 | 16.0 | | GAG | 28.7 | 33.8 |
| Gln | CAA | 21.6 | 20.1 | His | CAC | 8.7 | 15.6 | Asp | GAC | 17.0 | 29.1 |
| | CAG | 15.4 | 16.7 | | CAU | 13.1 | 10.7 | | GAU | 36.1 | 18.6 |
| Tyr | UAC | 13.6 | 19.7 | Gys | UGC | 7.7 | 8.6 | Phe | UUC | 17.9 | 27.3 |
| | UAU | 18.0 | 9.5 | | UGU | 10 | 6.7 | | UUU | 24.2 | 16.6 |

*The usage frequency of each codon comes from GenBank database; T represents tobacco and P represents potato virus.

At first, amplify the wide-type coat protein gene that does not contain any mutation, using the plasmid containing PVX coat protein gene as template. Insert the gene into the clone vector pBlueKS, between Xba I and Kpn I. As a result, pBCPW is constructed. In addition, five primers containing the restriction site and the corresponding mutation are designed (as shown in table 2).

EXAMPLE 2

Construction of the Plant Expression Vector Containing PVX Coat Protein Gene

Figure 1:
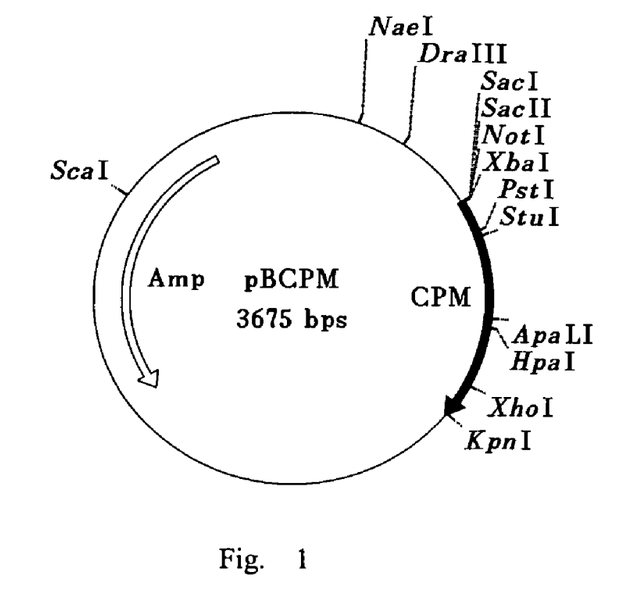
FIG. 1 is a graph showing the structure of the vector pBCPM.
Figure 2:
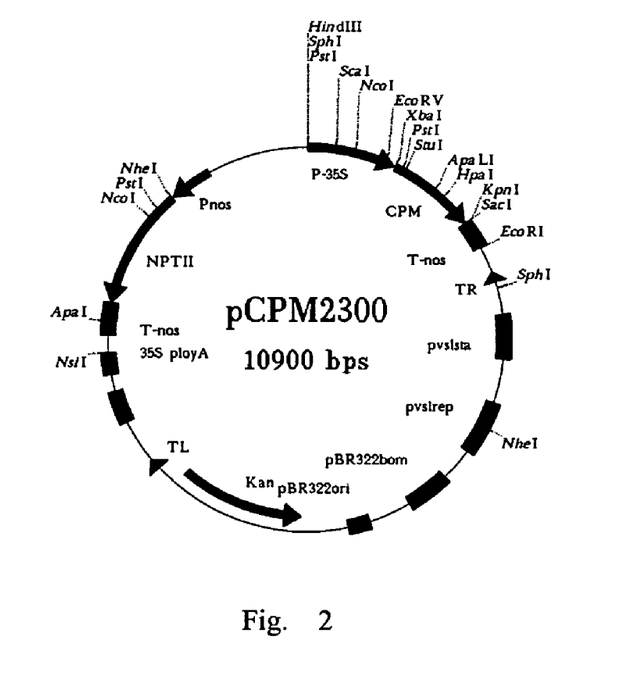
FIG. 2 is a graph showing the structure of the gene expression vector pCPM2300 of PVX coat protein, with the modifications of the codons.

Place the PVX coat protein gene with mutation(s), i.e., the pBCPM gene, under the control of the 35S promoter of the bases representing the new bases after the mutation, and SEQ ID NO: 2 in the sequence list is the mutated sequence. Each of the arrows represents one of the primers, as well as the direction of the specific primer. The shadow area indicates the recognition sequence of the restriction endonuclease that cuts the sequence at the right). Then, by using EcoR I and Hind III to digest pSPRCPM, the expression structure P35S-CPM-Tnos containing PVX coat protein gene is inserted into pCNPTII2300. As a result, the plant expression vector pCPM2300 is successfully constructed (the structural mapping is shown in FIG. 2). At the same time, the plant expression vector pCPW2300 containing the wide-type coat protein gene is constructed. With reference to the user's manual for the electroporation apparatus from BIO-DAD Company, of primers. The mutated coat protein gene, among the cloning vector, is designated as pBCPM (the schematic structural mapping is shown in FIG. 1). CaMV. (The specific sequence of the pBCPM gene is shown in FIG. 10. The single letter under each codon of the gene represents the corresponding amino acid. The bases to be mutated are indicated by boldface in the base sequence, and SEQ ID NO: 1 in the sequence list is the sequence to be mutated. Over the bases in boldface are transform these plant expression vectors into Agrobacterium tumefaciens LBA4404 through the electroporation procedure.

EXAMPLE 3

Obtaining the Transgenic Tobacco Plants

The *Agrobacterium tumefaciens* LBA4404 containing the plant expression vectors pCPM2300 and pCPW2300, is

TABLE 2

Primers for Site-directed Mutation of Coat Protein Gene

| Primer Number | Primer Sequence | | Restriction Endonuclease |
|---|---|---|---|
| Primer 1 | gctctagagatgtcagcaccagctagcacaac | (SEQ ID NO: 3) | Xba I |
| Primer 2 | ggggtaccctggtggtggtagagtgac | (SEQ ID NO: 4) | Kpn I |
| Primer 3 | gctctagagatgtcagcgccagcgagcacaac | (SEQ ID NO: 5) | Xba I |
| Primer 4 | aacaggcctgacgctgtcgcag | (SEQ ID NO: 6) | Stu I |
| Primer 5 | agtgtacacacctctttaatcgccgccgccag | (SEQ ID NO: 7) | ApaL I |
| Primer 6 | aaaactgcaggcgcgacgccggcgacagcgtc | (SEQ ID NO: 8) | Pst I |
| Primer 7 | gatgttaacgaacaactcgccgccggcgaactg | (SEQ ID NO: 9) | Hpa I |

Amplify the corresponding fragment containing the modifications of codon, with pBCPW as a template, through the Polymerase Chain Reaction (PCR) and the restriction endonuclease procedure. The resultant fragments, along with the non-mutation part of the coat protein gene and the vector, are constructed into the cloning vector through the ligation reaction of three fragments. The sequencing confirms that the ligation sequence of the construct is correct. Then, with the vector that is successfully mutated as a template, amplify the coat protein gene containing the modification codons at different sites in the gene, by using of the different combinations inoculated into 20 ml of YEB liquid culture medium (containing 50 mg/L of each of Km and Rif, respectively). Incubate overnight at 28° C. in the dark. In the next day, 2%-4% of the culture is transferred and inoculated into YEB culture medium without antibiotic (containing 100 μM/L of acetyl syringone). Incubate for 3 hours under strong shaking. Measure the OD value and dilute to the corresponding concentration (the value of OD is at about 0.5). Take a sterile tobacco leaf and cut it into a leaf disc. Add the culture liquid of *Agrobacterium tumefaciens* having the corresponding concentration to immerse the leaf disc for 3 to 5 minutes. Then, the leaf disc is re-inoculated into the co-culture medium, and cultured for 2 to 3 days at 28° C. in the dark. Then, by strict screening with 75 mg/L Kan, obtain the resistant buds. The obtained resistant buds take root on the culture medium containing 75 mg/L Kan and become whole plants with the resistance. When the plants grow out 3 to 4 euphylla, they are subjected to the open water culture. After the new roots come out, the plants are transferred into the greenhouse.

EXAMPLE 4

The Molecular Detection of the $T_0$ Generation Plant of Transgenic Tobacco

1. The Extraction of the Total DNA of Tobacco

Take 0.3 mg of the fresh tobacco leaves and place it into a mortar, grind into powders under the liquid nitrogen, transfer them into a centrifugal tube, and add 0.6 ml of CTAB buffer (30 g/L CTAB, 1.4 mol/L NaCl, 0.2% mercaptoethanol, 20 mmol/L EDTA and 100 mmol/L Tris-HCl, pH8.0) preheated at 60° C. into the tube. Incubate the tube at 60° C. for 30 min. During the period with the constant temperature of 60° C., gently shake the tube for several times. Then, add the equal volume of chloroform: isopentanol (24:1) to extract for one time. Transfer the supernatant to a new centrifugal tube and add ⅔-fold volume of isopropyl alcohol into the new centrifugal tube. The obtained precipitation is DNA. Add a little of the wash solution (the parts by volume are 76% ethanol, and 10 mmol/L NH$_4$Ac) to wash the precipitate for one time. After drying, dissolve the DNA with 500 μl TE buffer (10 mmol/L Tris-HCl (pH8.0), 1 mmol/L EDTA). Then, add RNase A (the final concentration is 10 mg/L) into the resultant solution and keep the temperature at 37° C. for 30 minutes. Following the treatment, extract once with equal volume of phenol, phenol:chloroform:isopentanol (25:24:1), and chloroform:isopentanol (24:1) in turn. Add 2.5-fold volume of absolute ethanol to the aqueous phase to precipitate the DNA. After drying, dissolve the DNA in 100 μl of sterile water.

1 PCR Analysis

Figure 3:
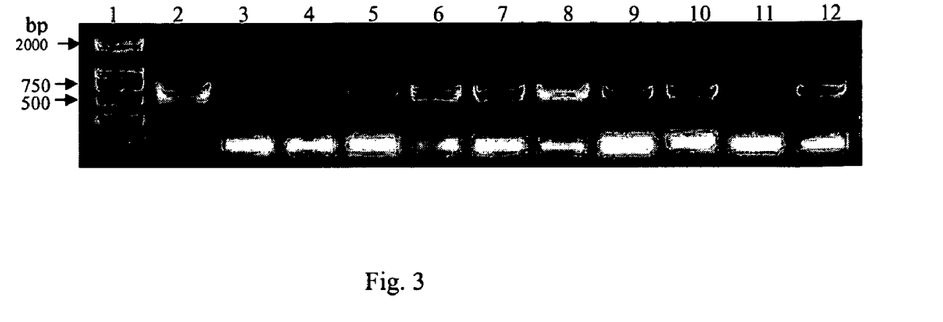
FIG. 3 is part of the electrophoresis result of PCR analysis for $T_0$ generation of tobacco plant transformed by pCPM2300 vector.

The PCR analysis is conducted with the plants differentiated from a total of 120 resistant clones of the $T_0$ generation of tobacco transformed by pCPW2300 (46 plants) and pCPM2300 (74 plants). Taking 1 μl of DNA as the template, carry out the PCR reaction. The 50-μl of reaction system includes: 5 μl of 10×PCR reaction buffer, 1 μl of 10 mM primer P1, 1 μl of 10 mM primer P2, 1 μl of DNA template, 4 μl of 2.5 mM dNTP and with a balance of the sterile water up to 50 μl total volume. The PCR reaction profile are as follows: pre-denature for 5 min at 94° C., denature for 1 min at 94° C., renature for 1 min at 52° C. and extend for 1.5 min at 72° C., for 30 cycles, and finally extend for 10 min at 72° C. Remove 10 μl of the PCR product to perform the gel electrophoresis analysis. The result is shown in FIG. 3. In this figure, Lane 1 is DL2000 Marker; Lane 2 is the positive control, the pCPISAPH2300 plasmid; Lane 3 is the negative control, the non-transgenic plant; and Lanes 4-12 are the transgenic plants transformed with the pCPISAPH vector. The results of PCR detection show that the tobacco plants that grow normal roots are all the plants transformed with the CP gene.

3. Extraction of the Total RNA of Tobacco

Take 1 g of fresh tobacco leaves, grind into powders under the liquid nitrogen, transfer them into a centrifugal tube and add 2 ml of denatured liquids to mix well. Then, add 0.1-fold volume of 2M NaAc (pH4.5) and mix well. Following this, add 1-fold volume of water-saturated phenol and mix well. And then, add 0.2 volume of chloroform:isopentanol (49:1) followed with a strong shaking until they are mixed evenly. The resultant mixture is subjected to ice bath for 15 min. Centrifuge for 20 min at 4° C., 10000 g. Extract the supernatant and add the equal volume of isopropyl alcohol into the supernatant. After a well mixing, place at −20° C. for 1 h. Then, centrifuge for 15 min at 4° C., 10000 g and discard the supernatant. After being re-suspended with a 4M LiCl, Centrifuge again. Dissolve the RNA precipitate with 2 ml of the DEPC treated water. Extract one time with the equal volume of water-saturated phenol, water-saturated phenol:chloroform, and chloroform, respectively. Finally, add 1/10 volume of 3M NaAc (pH5.4) and 2-fold volume of absolute alcohol into the supernatant, in order to precipitate RNA. Centrifuge for 15 min at 10,000 g and discard the supernatant. Wash the precipitate with 75% ethanol for one time, blow-dry the RNA precipitate and dissolve the RNA precipitate with 50 μl of water without RNase. Store the RNA solution at −70° C. for future use.

4. Northern Blot Analysis

Figure 4:
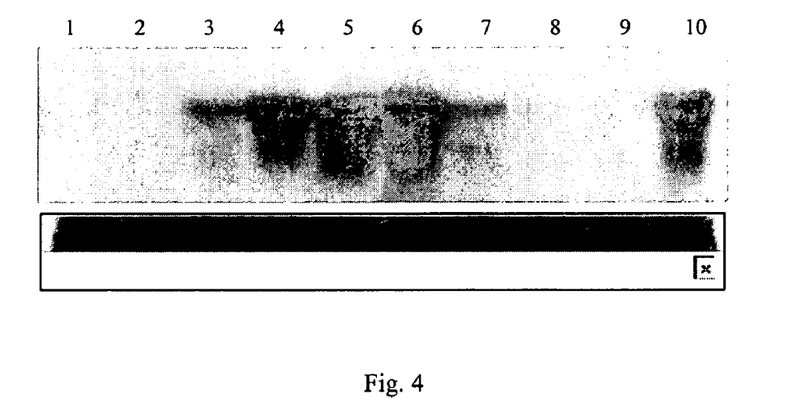
FIG. 4 is part of the Northern blot analysis for $T_0$ generation plant transformed by pCPM2300.
Figure 5:
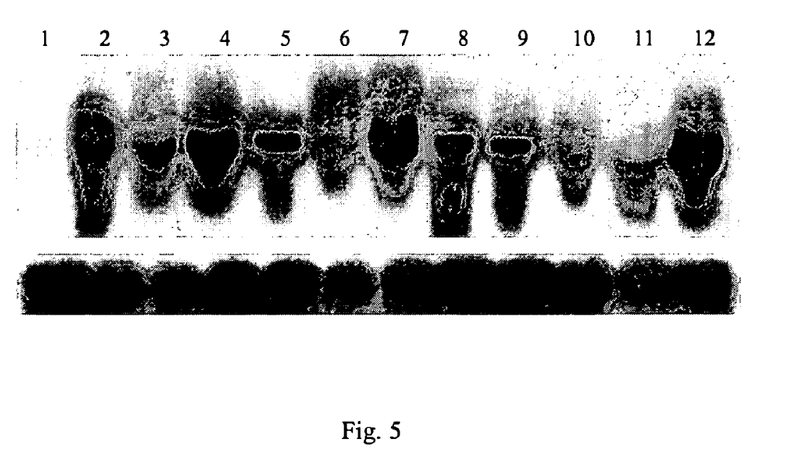
FIG. 5 is also part of the Northern blot analysis for $T_0$ generation plant transformed by pCPISAPH.

All the pCPM2300-transformed plants and some of the pCPW2300-transformed plants are used for performing the Northern blot analysis. Load 20 μg of RNA in 1.2% denatured gel to electrophoresis, until bromophenol blue moves to ¾ of the gel. Transfer the separated RNA onto the Hybond-N$^+$ membrane (Amersham pharmacia) with 20×SSC. After finishing the transfer, wash the membrane with the transferred substances in 2×SSC for one time, and fix the washed membrane at 80° C. under vacuum for 2 hours. The prehybridization is carried out in 0.5 M sodium phosphate buffer containing 7% SDS (W/V), at 65° C. for 2 hours. The labeling of probes is performed through the random primer method, using [α-$^{32}$P] dCTP (Amersham pharmacia) (The labeling reagent kit from Promega). Hybridize overnight at 65° C. After washing the membrane in 0.1×SSC at 65° C., press X-ray graphic and perform the radioactive self-development. The results are shown in FIG. 4 and FIG. 5. In FIG. 4, a: Lanes 1-8 represent the hybridized bands of the mutated coat protein gene (cp); and, b: 18s rRNA. In FIG. 5, a: Lane 1 represents the negative control of pCNPT-II, and Lanes 2-12 the hybridized bands of the non-mutation coat protein gene (cp); and, b: 18s rRNA. From the figures, it can be seen that the inactivation of the target genes occurs by the mutation of the coat protein genes (cp) (In FIG. 4, no hybridized band appears in Samples 1, 2, 8 and 9), and that the level of the mRNA amount of the cp gene is obviously lower than that of the mRNA amount of the un-mutated coat protein gene (cp).

EXAMPLE 5
In Vitro Transcription and Inoculating Virus into the Transgenic Tobacco 1. In Vitro Transcription of the PVX Virus Vector The pP2C2S PVX virus vector is purified through passing the column of the Promega plasmid purification kit. After the resultant vector is linearized by digestion with enzyme Spe I, begin to perform in vitro transcription with using the Promega in vitro transcription kit. At first, add the in vitro transcription buffer in a microfuge tube. Then, in the following order, add ATP, UTP, CTP (2 mM for each), 0.2 mM GTP, 0.5 mM cap m7G(5')PPP(5')G, RNase inhibitor (Pharmacia), linearized DNA and T7RNA polymerize enzyme into the microfuge tube containing the transcription buffer. Incubate the reaction for 30 min at 37° C. Again, add GTP up to the final concentration of 2 mM and incubate for 1 h at 37° C. Extract the product with water-saturated phenol/chloroform. Add 1/10 volume of NaAc (pH5.4) and 2-fold volume of absolute alcohol to precipitate RNA, thereby obtain PVX RNA virus.

2. Mechanical Inoculation of Virus

The obtained PVX RNA virus is mechanically exposed to $T_0$ generation plant of the transgenic tobacco transformed with pCPW2300 and pCPM2300. Before the infection, the RNA precipitate prepared by in vitro transcription is dissolved into 35 μl of water (DEPC-treated, containing 50 mM phosphoric acid buffer, pH 7.0 and 5 μg/μl bentonite). Spread the PVX virus onto the tobacco leaves that have been gently polished with carborundum (600 grit Carborundum). The infected tobacco is incubated for 16 h under light and then for 8 hours at 20° C. in the dark, and finally at 25° C. Observe each of the plants and note the symptoms produced by the virus infection. The result is shown in Table 3 and FIGS. 6-9.

TABLE 3

The occurrence percentage of each symptom of the infected tobacco

| | | | The infected symptom of the transgenic tobacco | | | |
|---|---|---|---|---|---|---|
| | Number | | Recovery happens | | | |
| Types of the transgenic tobacco | of the infected plants | Complete immunity | Highly resistant (%) | Moderately resistant (%) | No recovery happens | Rate of recovery (%) |
| Transgenic tobacco transformed with the modified coat protein gene (CPM) | 33 | 8 | 10 (30.3%) | 12 (36%) | 3 | 73 |
| Transgenic tobacco transformed with the non-modified wide-type coat protein gene (CPW) | 30 | 4 | 6 (20%) | 10 (33%) | 10 | 53 |
| Control tobacco transformed with the empty vector | 10 | None | 0 | 1 (10%) | 9 | 10 |

Figure 6:
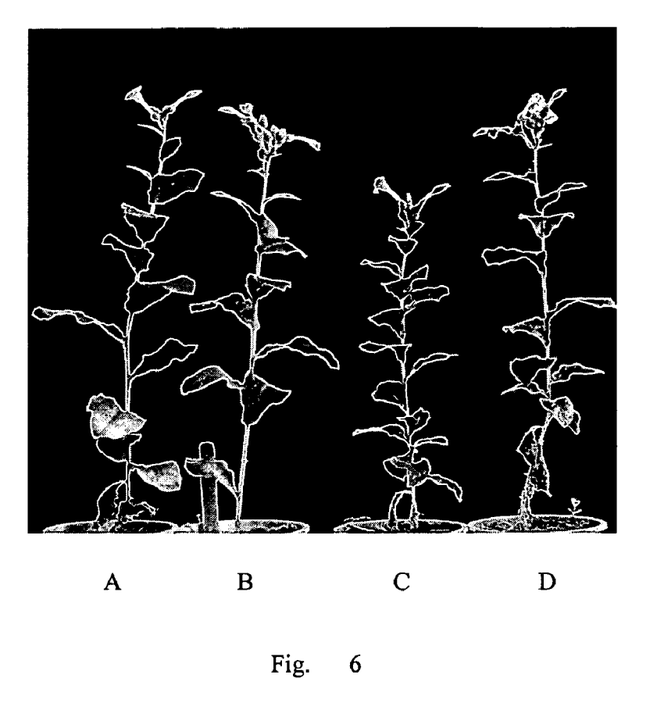
FIG. 6 is the comparison results of the PVX symptoms, following the inoculation of the virus.
Figure 7:
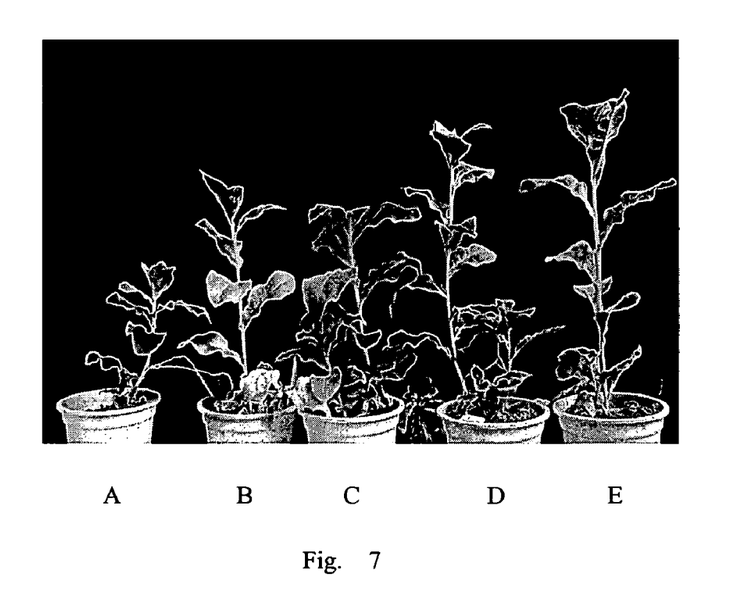
FIG. 7 is the comparison results of the recovery symptoms.
Figure 8:
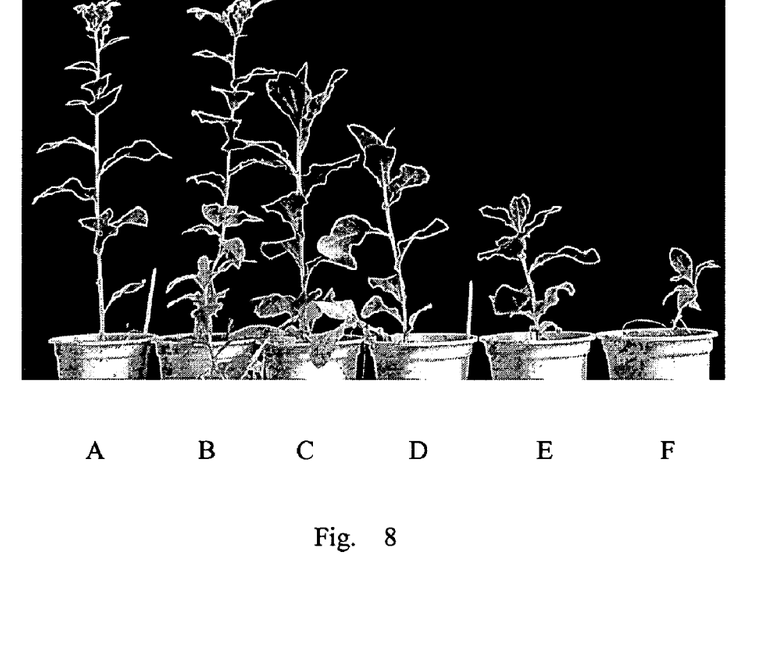
FIG. 8 is the comparison of the symptoms.
Figure 9:
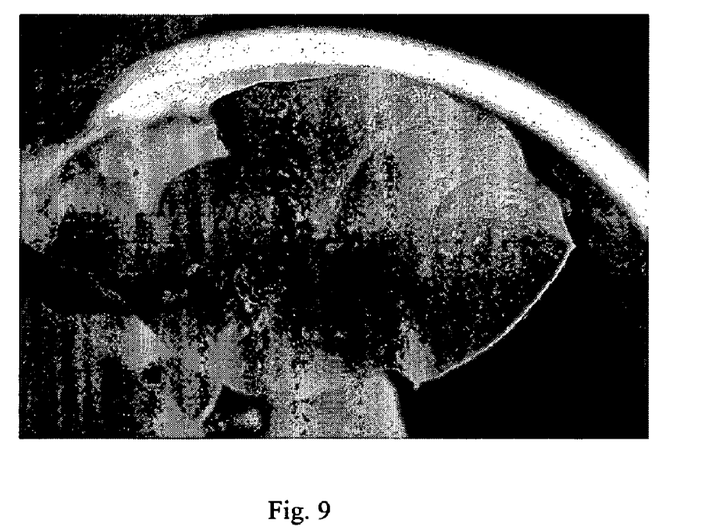
FIG. 9 is the symptoms on the leaf from the infected plant.

In FIG. 6, the reference signs refer to the following: A for the non-transgenic plant without the inoculation of virus, B for the pCPM2300-transformed plant without the inoculation of virus, C for the pCPM2300-transformed plant exhibiting the immunity symptom due to the inactivation of the cp gene, D for the pCPM2300-transformed plant exhibiting the highly resistant symptom due to the weak expression of the cp gene. In FIG. 7, the reference signs refer to the following things: A for the non-transgenic plant, B and C for the transgenic plant with pCPW2300, and D and E for the transgenic plant with pCPM2300. In FIG. 8, the reference signs refer to the following things: A for the highly resistant symptom of the pCPW2300 transgenic plant, B for the highly resistant symptom of the pCPM2300 transgenic plant, C for the recovery symptom of the pCPM2300 transgenic plant, D for the recovery symptom of the pCPM2300 transgenic plant, E for the recovery symptom of the non-transgenic plant, and F for the infection symptom of the non-transgenic plant. Form the data in Table 3 and the results in FIGS. 6-9, it can be seen that there are more plants exhibiting the complete immunity or the highly resistant symptom in the transgenic plants of tobacco with the inactivation of the cp gene, compared with the transgenic plants with the non-inactivation of the cp gene. This demonstrates the effectiveness of this method in breeding the high antiviral plants.

The present invention conducts a replacement of certain codons in the coat protein (cp) gene of potato X virus with the synonymous rare codons, in order to let the gene contain more rare codons. The transformation vector is constructed, and the plants of tobacco are transformed. Molecule detection is used to determine the expression of the gene cp. The detection result shows that the inactivation rate in the plants of tobacco transformed with the non-modified cp gene is 6.25%, while the tobacco transformed with the codon-modified cp gene has 35% of the cp genes inactivated. The ELISA result shows that the protein expression level of the tobacco plants containing the codon-modified cp gene is significantly lower than the protein expression level led by the cp gene without the codon modification. This shows that the method according to the present invention shut off genes effectively. The result of the mechanical inoculation of transgenic tobacco with virus indicates that there are more plants that show the symptom of complete immunity or high resistance among the transgenic tobacco plants in which the inactivation of the gene cp occurs, compared with the transgenic tobacco plants in which the inactivation of the gene cp does not happen. This proves that the method according to the present invention has the utility in the field of breeding high antiviral plants.

What is claimed is:

1. A method for producing transgenic plants with high antiviral property, comprising the following steps of:
    a. checking the frequency of codon usage in a host and determining synonymous codons with a usage frequency of 0-10% in the host, modifying the codons in a coat protein gene of the Potato Virus X so that some codons in said gene are mutated into the synonymous codons in the host plant;
    b. constructing a vector containing said gene with the codon modifications, to be used for transforming plants;
    c. transforming the plants with the recombinant vector to obtain the regenerative transgenic plants; and
    d. detecting the transformed plants, screening the transgenic plants in which a gene silencing occurs in said gene, and thereby obtaining the transgenic plants with high antiviral property.

2. The method for producing transgenic plants with high antiviral property of claim 1, wherein said vector further comprises a selective marker gene.

3. The method for producing transgenic plants with high antiviral property of claim 1 or claim 2, wherein said vector is a binary vector.

4. A plant cell line obtained from the method of claim 1.

5. A plant obtained from the method of claim 1.

* * * * *

SEQUENCE LISTING

```
<160> NUMBER OF SEQ ID NOS: 9

<210> SEQ ID NO 1
<211> LENGTH: 731
<212> TYPE: DNA
<213> ORGANISM: Potexvirus, Potato virus X

<400> SEQUENCE: 1
gctctagaga tgtcagcacc agctagcaca acacagccca tagggtcaac tacctcaact      60
accacaaaaa ctgcaggcgc aactcctgcc acagcttcag gcctgttcac catcccggat     120
ggggatttct ttagtacagc ccgtgccata gtagccagca atgctgtcgc aacaaatgag     180
gacctcagca agattgaggc tatttggaag gacatgaagg tgcccacaga cactatggca     240
```

```
caggctgctt gggacttagt cagacactgt gctgatgtag gatcatccgc tcaaacagaa      300
atgatagata caggtcccta ttccaacggc atcagcagag ctagactggc agcagcaatt      360
aaagaggtgt gcacacttag caatttttgc atgaagtatg ctccagtggt atggaactgg      420
atgttaacta acaacagtcc acctgctaac tggcaagcac aaggtttcaa gcctgagcac      480
aaattcgctg cattcgactt cttcaatgga gtcaccaacc cagctgccat catgcccaaa      540
gaggggctca tccggccacc gtctgaagct gaaatgaatg ctgcccaaac tgctgccttt      600
gtgaagatta caaaggccag ggcacaatcc aacgactttg ccagcctaga tgcagctgtc      660
actcgaggtc gtatcactgg aacaacaacc gctgaggctg ttgtcactct accaccacca      720
taaggtaccc c                                                          731

<210> SEQ ID NO 2
<211> LENGTH: 731
<212> TYPE: DNA
<213> ORGANISM: Artificial sequence
<220> FEATURE:
<223> OTHER INFORMATION: PVX coat protein gene with mutation

<400> SEQUENCE: 2
gctctagaga tgtcagcgcc agcgagcaca acacagccca tagggtcaac tacctcaact       60
accacaaaaa ctgcaggcgc gacgccggcg acagcgtcag gcctgttcac catcccggat      120
ggggatttct ttagtacagc ccgtgccata gtagccagca atgctgtcgc aacaaatgag      180
gacctcagca agattgaggc tatttggaag gacatgaagg tgcccacaga cactatggca      240
caggctgctt gggacttagt cagacactgt gctgatgtag gatcatccgc tcaaacagaa      300
atgatagata caggtcccta ttccaacggc atcagcagag ctagactggc ggcggcgatt      360
aaagaggtgt gcacacttag caatttttgc atgaagtatg ctccagtggt atggaactgg      420
atgttaacga acaactcgcc gccggcgaac tggcaagcac aaggtttcaa gcctgagcac      480
aaattcgctg cattcgactt cttcaatgga gtcaccaacc cagctgccat catgcccaaa      540
gaggggctca tccggccacc gtctgaagct gaaatgaatg ctgcccaaac tgctgccttt      600
gtgaagatta caaaggccag ggcacaatcc aacgactttg ccagcctaga tgcagctgtc      660
actcgaggtc gtatcactgg aacaacaacc gctgaggctg ttgtcactct accaccacca      720
taaggtaccc c                                                          731

<210> SEQ ID NO 3
<211> LENGTH: 32
<212> TYPE: DNA
<213> ORGANISM: Artificial sequence
<220> FEATURE:
<223> OTHER INFORMATION: Primer

<400> SEQUENCE: 3
gctctagaga tgtcagcacc agctagcaca ac                                    32

<210> SEQ ID NO 4
<211> LENGTH: 27
<212> TYPE: DNA
<213> ORGANISM: Artificial sequence
<220> FEATURE:
<223> OTHER INFORMATION: Primer

<400> SEQUENCE: 4
ggggtaccct ggtggtggta gagtgac                                          27
```

```
<210> SEQ ID NO 5
<211> LENGTH: 32
<212> TYPE: DNA
<213> ORGANISM: Artificial sequence
<220> FEATURE:
<223> OTHER INFORMATION: Primer

<400> SEQUENCE: 5
gctctagaga tgtcagcgcc agcgagcaca ac                                     32

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
aacaggcctg acgctgtcgc ag                                                22

<210> SEQ ID NO 7
<211> LENGTH: 32
<212> TYPE: DNA
<213> ORGANISM: Artificial sequence
<220> FEATURE:
<223> OTHER INFORMATION: Primer

<400> SEQUENCE: 7
agtgtgcaca cctctttaat cgccgccgcc ag                                     32

<210> SEQ ID NO 8
<211> LENGTH: 32
<212> TYPE: DNA
<213> ORGANISM: Artificial sequence
<220> FEATURE:
<223> OTHER INFORMATION: Primer

<400> SEQUENCE: 8
aaaactgcag gcgcgacgcc ggcgacagcg tc                                     32

<210> SEQ ID NO 9
<211> LENGTH: 33
<212> TYPE: DNA
<213> ORGANISM: Artificial sequence
<220> FEATURE:
<223> OTHER INFORMATION: Primer

<400> SEQUENCE: 9
gatgttaacg aacaactcgc cgccggcgaa ctg                                    33
```